United States Patent

Halmos

[11] 4,239,912
[45] Dec. 16, 1980

[54] PROCESS FOR RESOLVING DL-MANDELIC ACID WITH NOVEL 2-BENZYLAMINO-1-BUTANOLS

[75] Inventor: Imre A. Halmos, Summit, N.J.

[73] Assignee: American Cyanamid Company, Stamford, Conn.

[21] Appl. No.: 968,041

[22] Filed: Dec. 8, 1978

Related U.S. Application Data

[63] Continuation of Ser. No. 831,024, Sep. 6, 1977, abandoned.

[51] Int. Cl.³ .............................................. C07B 19/00
[52] U.S. Cl. ................................ 562/401; 260/501.11; 562/470
[58] Field of Search ............................ 562/401, 470; 260/501.11

[56] References Cited

U.S. PATENT DOCUMENTS

| | | | |
|---|---|---|---|
| 2,243,977 | 6/1941 | Peyer | 260/570.6 |
| 2,597,248 | 5/1952 | Kerwin et al. | 260/570.6 |
| 2,820,827 | 1/1958 | Ruschig et al. | 260/570.6 |
| 2,921,959 | 1/1960 | Amiard et al. | 562/401 |
| 3,655,743 | 4/1972 | Nickl et al. | 562/470 X |
| 3,725,465 | 4/1973 | Stoeck et al. | 260/501.11 |
| 3,739,019 | 6/1973 | Ueda et al. | 562/401 |
| 3,803,213 | 4/1974 | Weber et al. | 562/401 X |
| 4,002,666 | 1/1977 | Shirai et al. | 562/401 X |

Primary Examiner—Natalie Trousof
Assistant Examiner—Vera C. Clarke
Attorney, Agent, or Firm—Jack W. Richards

[57] ABSTRACT

A process for resolving DL-Mandelic acid which comprises reacting at moderately elevated temperatures in a two-phase liquid mixture of water and a suitable water-immiscible organic solvent about equimolecular amounts of DL-Mandelic acid and an optically active 2-benzylamino-1-butanol, represented by formula (I),

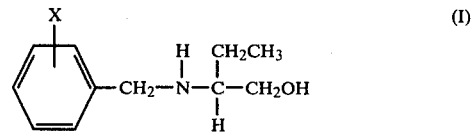

to form a crude mandelate salt, represented by formula (II),

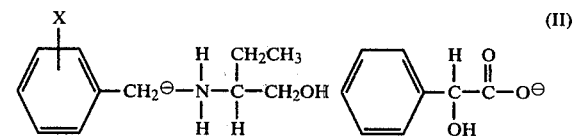

wherein X is chloro, bromo, fluoro, or nitro; said crude mandelate salt is recovered and purified by contact with a suitable solvent to obtain an optically pure mandelate salt, represented by formula (II); the optically active mandelate salt is hydrolyzed with aqueous sodium or potassium hydroxide in a two-phase liquid mixture to obtain an organic phase containing an optically active compound of formula (I) and an alkalized aqueous phase containing the sodium or potassium salt of an optically active mandelic acid. The latter is acidified and an optically active mandelic acid is recovered therefrom.

6 Claims, No Drawings

PROCESS FOR RESOLVING DL-MANDELIC ACID WITH NOVEL 2-BENZYLAMINO-1-BUTANOLS

This is a continuation, of application Ser. No. 831,024, filed Sept. 6, 1977 now abandoned.

BACKGROUND OF THE INVENTION

The invention relates to a new process for the resolution of DL-Mandelic acid. More particularly, it relates to a process for the resolution of DL-Mandelic acid in a two-phase liquid medium by the use of novel optically active 2-benzylamino-1-butanols.

The novel optically active 2-benzylamino-1-butanols which are useful in this process are represented by Formula (I),

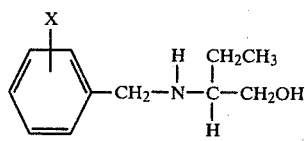

wherein X represents chloro, bromo, fluoro, nitro or methyl. A related pending application, to a process for the resolution of DL-mandelic acid, is U.S. Application Ser. No. 18,695 filed Mar. 8, 1979 which is a continuation application of U.S. application Ser. No. 831,025 filed Sept. 6, 1977 now abandoned.

The use of optically active amines such as quinine, (−)-α-(1-naphtyl)ethylamine, (+)-2-amino-1-butanol, (−)-menthylamine, and the like, to resolve racemic mixtures of carboxylic acids, such as tartaric acid, mandelic acid, aspartic acid, and the like, is well known in the art.

Applicants are not aware of any prior art reference which, in their respective judgements as one skilled in the art of resolving DL-Mandelic acid, would anticipate or render obvious the novel process of the instant invention; however, for the purpose of fully developing the background of the invention and establishing the state of the requisite art, the following references are set forth: Germ. Offen. 2,007,177 which discloses the formation of an optically active ammonium salt by reaction of the dextro- or levo-rotatory 2-(benzylamino)-1-propanol and cleavage of the said ammonium salt with dilute hydrochloric acid to recover the optically active acid. An English language abstract of this reference is contained in Chem. Abs. 73, 120417 (1970). U.S. Pat. No. 3,553,257 which discloses the preparation of dextrorotatory 2-amino-1-butanol. Beilstein 4, 291 which discloses the preparation of levo-rotatory 2-amino-1-butanol.

Since none of the known optically active amines has been found to be completely satisfactory, research continues in order to find new compounds and processes which will be more satisfactory. The present invention arose out of such research and resulted in surprising discovery that racemic mixtures of mandelic acid can be readily resolved in a two-phase liquid mixture of water and a water-immiscible organic solvent with the compounds of formula (I). The process of this invention is useful for the resolution of racemic mixtures of mandelic acid. The utility of D-(−)-mandelic acid and its derivatives, or L-(+)-mandelic acid is known in the art. See, eg., Germ. Offen. 2,415,402 and Germ. Offen. 2,436,686, an English language abstract of which is disclosed in Chem. Abs. 82, 31343m (1975) and Chem. Abs. 83, 10556 p (1975), respectively.

SUMMARY OF THE INVENTION

In accordance with the present invention there is provided a process for resolving DL-Mandelic acid which comprises reacting at moderately elevated temperatures in a two-phase liquid mixture of water and a suitable water-immiscible organic solvent about equimolecular amounts of DL-Mandelic acid and an optically active 2-benzylamino-1-butanol, represented by formula (I), to form a crude mandelate salt, represented by formula (II),

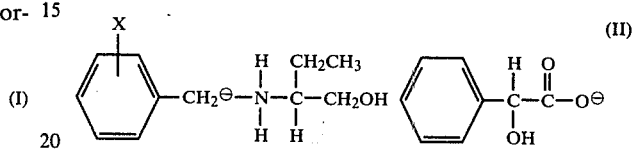

wherein X is as previously defined; said crude mandelate salt is recovered and purified by contact with a suitable solvent to obtain an optically pure mandelate salt, represented by formula (II); the optically active mandelate salt is hydrolyzed with aqueous sodium or potassium hydroxide in a two-phase liquid mixture to obtain an organic phase containing an optically active compound of formula (I) and an alkalized aqueous phase containing the sodium or potassium salt of an optically active mandelic acid. The latter is acidified and an optically active mandelic acid is recovered therefrom. This process comprises the following steps:

(a) reacting about equimolecular amounts of DL-mandelic acid and an optically active 2-benzylamino-1-butanol represented by formula (I),

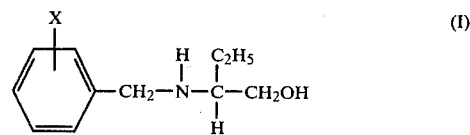

wherein X represents chloro, bromo, fluoro, or nitro, at moderately elevated temperatures in a two-phase mother liquor consisting of a mixture of an aqueous phase and an organic phase, said organic phase being a lower alkyl ester of a lower aliphatic carboxylic acid selected from ethyl acetate, n-propyl acetate, isopropyl acetate, ethyl propionate, n-propyl propionate, or isopropyl propionate, or mixtures thereof, to form a mandelate salt represented by formula (II),

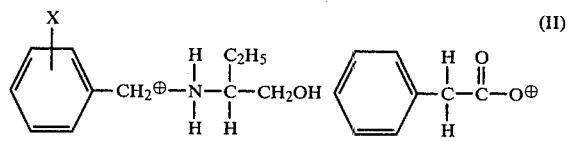

(b) cooling the reaction mixture to crystallize said mandelate salt;

(c) separating the crude mandelate salt from the two-phase mother liquor;

(d) recrystallizing or slurrying the crude mandelate salt in a solvent medium selected from water, methanol, ethanol, or isopropanol, or mixtures thereof, to obtain an optically pure mandelate salt;

(e) alkalizing the equeous phase of the two-phase mother liquor obtained in step (c);

(f) separating the alkalized aqueous phase from the organic phase;

(g) agitating the optically pure mandelate salt from step (d) and the organic phase from step (f) with about 1.05 to 1.10 moles of aqueous sodium or potassium hydroxide per mole of mandelate salt at ambient temperature to hydrolyze said salt and form a clear two-phase liquid mixture consisting of an organic phase containing an optically active compound of formula (I) and an alkalized aqueous phase containing the sodium or potassium salt of an optically active mandelic acid;

(h) recovering the aqueous phase from step (g) and reacting said salt of an optically active mandelic acid with about an equimolecular amount of an organic dicarboxylic acid selected from oxalic, tartaric, maleic, malonic, or fumaric acid, at ambient or slightly elevated temperature to form a mixture of an optically active mandelic acid and a mono-sodium or potassium salt of said dicarboxylic acid having a low solubility in water;

(i) cooling the reaction mixture to ambient temperature and diluting the same with a water-soluble organic liquid solvent selected from acetone, methanol, ethanol, n-propanol, or isopropanol to complete the precipitation of said salt of said dicarboxylic acid;

(j) separating said salt of said dicarboxylic acid;

(k) removing said water-soluble organic solvent; and (l) recovering D-(−) or L-(+)-mandelic acid from said mother liquor.

In the preferred embodiment of this invention X represents chloro, bromo, or fluoro and the water-immiscible organic solvent is a lower alkyl ester of a lower aliphatic acid selected from ethyl acetate, n-propyl acetate, isopropyl acetate, ethyl propionate, n-propyl propionate or isopropyl propionate. The process of the preferred embodiment comprises performing the steps described in the above paragraph wherein step (a) is reacting equimolecular amounts of DL-mandelic acid and a compound of formula (I) wherein X represents chloro, bromo, or fluoro at a temperature of about 40°–50° C. in a mixture of water and isopropyl acetate; step (b) is cooling to a temperature of about 0°–25° C. over a period of about 1–2 hours; step (d) is slurrying said crude mandelate salt in water at an ambient or slightly elevated temperature and then cooling it to about 0°–20° C.; step (e) is alkalizing the aqueous phase of said two-phase mother liquor to a pH of at least 12; step (g) is agitating said optically pure mandelate salt and said organic phase with an amount of 50% by weight aqueous sodium hydroxide to provide between about 5–10% molecular excess of said sodium hydroxide after complete hydrolysis of said mandelate salt; step (h) is reacting said salt of an optically active mandelic acid with an equimolecular amount of oxalic acid at a temperature of about 25°–40° C.; and step (i) is cooling the reaction mixture to a temperature of about 20°–25° C. diluting the same with acetone to complete the precipitation of monosodium oxalate and cooling the essentially acetone-free mother liquor to a temperature of about 0°–10° C. to crystallize D-(−) or L-(+)-mandelic acid.

In the especially preferred embodiment of this invention the compound of formula (I) is D-(−)-2-(4-chlorobenzylamino)-1-butanol, and the water-immiscible organic solvent is isopropyl acetate. The process of the especially preferred embodiment comprises performing the steps described in the above two paragraphs wherein step (a) is reacting about equimolecular amounts of DL-mandelic acid and D-(−)-2-(4-chlorobenzylamino)-butanol; step (b) is cooling to a temperature of about 5°–10° C.; step (d) is slurrying said crude mandelate salt at a temperature of about 25°–30° C. and cooling it to about 5°–10° C. to obtain D-(−)-2-(4-chlorobenzylamino)-1-butanol-(−)-mandelate; step (e) is alkalizing said aqueous phase to a pH of about 13; step (g) is agitating said D-(−)-2-(4-chlorobenzylamino)-1-butanol-(−)-mandelate and said organic phase; step (h) is reacting at a temperature of about 30°–35° C.; and step (i) is cooling the reaction mixture to a temperature of about 20°–25° C. and diluting the same with acetone to complete the precipitation of monosodium oxalate and cooling the essentially acetone-free mother liquor to a temperature of about 0°–5° C. to crystallize D-(−)-mandelic acid.

The process of this invention is characterized by a unique two-phase liquid reaction medium which lends itself to the recovery of the crude mandelate salt, and the recovery and recycling of the optically active 2-benzylamino-1-butanol and unreacted mandelic acid.

In an alternative embodiment, this process comprises the steps described in the above paragraphs wherein step (f) is separating the alkalized aqueous phase from the organic phase, heating said aqueous phase at reflux temperature until racemization is complete and acidifying the resulting solution.

In a further alternative embodiment, this process comprises the steps described in the above paragraphs wherein step (f) is separating the alkalized aqueous phase from the organic phase, heating said aqueous phase at reflux temperature until racemization is complete and acidifying the resulting solution, and in a still further alternative embodiment, the DL-mandelic acid used in step (a) is obtained from the racemized aqueous phase of step (f).

In a final alternative embodient, this process comprises the steps described in the above paragraphs wherein the optically active 2-(benzylamino)-1-butanol used in step (a) is obtained from said organic phase containing an optically active compound of formula (I) of step (g).

DESCRIPTION OF PREFERRED EMBODIMENTS

The process of this invention may be divided into the following stages:

(1) the formation and isolation of a crude 2-benzylamino-1-butanol mandelate salt represented by formula (II), (2) the purification of the crude mandelate salt to obtain an optically pure mandelate salt also represented by formula (II), (3) the hydrolysis of the optically pure mandelate salt to form a sodium or potassium salt of an optically active mandelic acid, and (4) the recovery of an optically active mandelic acid from the solution containing said sodium or potassium salt.

The above-mentioned stages are described below in detail.

(1) Formation and Isolation of Crude Mandelate Salt

An aqueous solution containing about 4–17% by weight, preferably about 8–13%, of DL-Mandelic acid is agitated with a suitable water-immiscible organic solvent, in which the compound of formula (I) is soluble, preferably a lower alkyl ester of a lower aliphatic carboxylic acid, such as isopropyl acetate. About 1–3 parts by volume, preferably about 1.25–1.5 parts by volume, of organic solvent are employed per part by volume of aqueous solution.

About an equimolecular amount of a compound of formula (I) is added and the reaction mixture is heated to about 40°–55° C., preferably about 45°–50° C., and then cooled to about 0°–20° C., preferably about 5°–10° C., over a period of about 1–3 hours, preferably about 1–2 hours, to precipitate the desired mandelate salt. Preferably, the reaction mixture is seeded at about 20°–35° C. with a few crystals of the desired mandelate salt to induce crystallization. The crystals are then recovered and washed successively with the water-immiscible organic solvent and water at ambient temperatures. The washings are combined with the two-phase mother liquor.

Suitable water-immiscible organic solvents which may be used in the process of this invention include ethyl acetate, n-propyl acetate, isopropyl acetate, ethyl propionate, and n-propyl propionate, or mixtures thereof. The preferred organic solvent is isopropyl acetate.

The aqueous solution of DL-Mandelic acid may be prepared by acidifying a solution of sodium DL-mandelate to a pH of about 1.5–4.0, preferably about 1.8–3.8, at about ambient temperature.

Suitable inorganic acids which may be used in the acidification include concentrated hydrochloric acid, about 40–70% sulfuric acid, phosphoric, concentrated hydrobromic acid, and the like.

Illustrative examples of compounds of formula (I) which may be used in the process of this invention include the following:

D-(−)- or L-(+)-2-(4-chlorobenzylamino)-1-butanol,
D-(−)- or L-(+)-2-(4-bromobenzylamino)-1-butanol,
D-(−)- or L-(+)-2-(4-fluorobenzylamino)-1-butanol,
D-(−)- or L-(+)-2-(3-chlorobenzylamino)-1-butanol,
D-(−)- or L-(+)-2-(3-fluorobenzylamino)-1-butanol,
D-(−)- or L-(+)-2-(3-bromobenzylamino)-1-butanol,
D-(−)- or L-(+)-2-(2-chlorobenzylamino)-1-butanol,
D-(−)- or L-(+)-2-(2-bromobenzylamino)-1-butanol,
D-(−)- or L-(+)-2-(2-fluorobenzylamino)-1-butanol,
D-(−)- or L-(+)-2-(4-nitrobenzylamino)-1-butanol,
D-(−)- or L-(+)-2-(3-nitrobenzylamino)-1-butanol,
D-(−)- or L-(+)-2-(2-nitrobenzylamino)-1-butanol, (2) Purification of Crude Mandelate Salt The crude mandelate salt of (1) may be purified by recrystallizing it from a suitable solvent such as water or a water-miscible organic solvent such as methanol, ethanol, or isopropanol, or mixtures thereof. Preferably, the purification is carried out by slurrying about 1.5–2 parts by weight of water with one part by weight of crude mandelate at about 25°–55° C., preferably about 25°–30° C., and cooling the slurry to about 0°–20° C., preferably about 5°–10° C., to crystallize the desired optically active mandelate salt. The crystals are then recovered, rinsed with ice cold water (about 3°–5° C.) and dried to obtain the mandelate salt in a yield about 84% of theoretical based on starting material.

The mother liquor and wash liquor from the purification is combined with the two-phase liquid mixture obtained in (1) and alkalized with sodium or potassium hydroxide, preferably sodium hydroxide, to increase the pH of the aqueous layer to at least 12, preferably about 13.

The alkalized aqueous phase, now containing the sodium or potassium salt of the undesired mandelic acid, is separated and reserved for subsequent racemization.

The organic phase is reserved for the hydrolysis step. Optionally the organic phase can be washed with water before hydrolyzing.

(3) Hydrolysis of Optically Active Mandelate Salt

The purified mandelate salt from (2) is agitated with the organic phase recovered in (2), preferably isopropyl acetate, and an aqueous solution of an alkalizing agent, preferably a dilute solution of caustic soda containing about 1.05–1.10 moles of sodium hydroxide per mole of mandelate salt, at about 20°–30° C., preferably about 25°–30° C., until the two-phase mixture becomes clear. The aqueous phase now contains an alkali salt of the desired mandelic acid and the organic phase contains practically all of the compound of formula (I) charged in (1).

The aqueous phase is recovered and optionally reextracted with additional water-immiscible organic solvent, preferably isopropyl acetate.

(4) Recovery of Optically Active Mandelic Acid

The aqueous phase from (3) is stirred with about an equimolecular amount of a suitable dicarboxylic acid, preferably oxalic acid dihydrate, at about 25°–50° C., preferably about 30°–35° C., to form a solution containing the desired optically active mandelic acid. The solution is cooled to ambient temperature to precipitate an alkali acid salt, preferably sodium acid oxalate, therefrom. The resulting slurry is then diluted with a water-miscible organic solvent to complete the precipitation of the alkali acid salt.

Suitable dicarboxylic acids which may be used include oxalic acid dihydrate, tartaric, maleic, fumaric and malonic acids, and the like.

Suitable water-miscible organic solvents which may be used include methanol, ethanol, isopropanol, n-propanol or acetone, or mixtures thereof. The preferred diluent is acetone. Generally about 1–3 volumes of diluent are employed per volume of aqueous solution.

The alkali acid salt is separated and the mother liquor is heated to distil off the water-miscible organic solvent. The residual solution is then cooled to about 0°–10° C., preferably about 0°–5° C., stirred thereat for about one hour and filtered. The crystals are rinsed with ice cold water, about 3°–5° C., and dried to obtain D-(−) or L-(+)-mandelic acid. The overall yield from (1) is about 60% of theoretical. Further amounts of the optically active mandelic acid can be recovered by concentrating the aqueous filtrate.

Racemization and Recovery of DL-Mandelic Acid

The alkalized aqueous phase from (2) which contains the sodium or potassium salt of the undesired mandelic acid is further alkalized by the addition thereto of about two moles of additional sodium or potassium hydroxide per mole of mandelic acid therein. The reaction mixture is then heated at reflux until racemization is completed, as indicated by a zero optical rotation. The reaction mixture is then neutralized to pH 7 by the addition of concentrated hydrochloric acid and at least an equivalent amount of calcium chloride is added. The resulting calcium DL-mandelate which precipitates is recovered by filtration, washed with water and reacted in water with an equimolecular amount of sodium carbonate. The precipitated calcium carbonate is recovered by filtration and the resulting filtrate containing sodium DL-mandelate is acidified, as previously described, and recycled in (1).

The calcium DL-mandelate may also be reacted in water with an equimolecular amount of a dicarboxylic acid such as oxalic acid dihydrate, tartaric, maleic, fumaric, and malonic acids, and the like, to form an insoluble calcium salt of the dicarboxylic acid and an aqueous solution containing DL-mandelic acid. The insoluble salt is separated by filtration and the aqueous filtrate is recycled in (1).

The optically active 2-(benzylamino)-1-butanol compounds used in this invention may be prepared by two methods. In one method, an optically active form of 2-amino-1-butanol is reacted with an appropriate benzyl halide (III), as illustrated below, wherein X is as previously defined, and Y is a halogen atom, such as chloro, bromo, or fluoro.

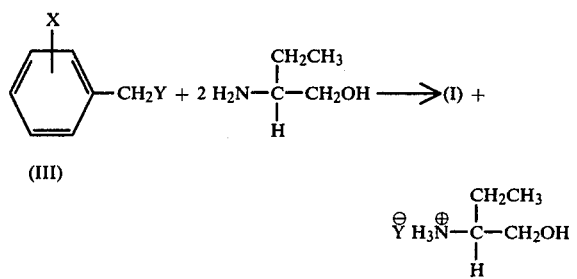

In the above reaction sufficient excess (+)- or (−)-2-amino-1-butanol is employed to react with any hydrogen halide generated in the reaction. The reaction is carried out by adding the benzyl halide in portions to the (+)- or (−)-2-amino-1-butanol at about 60° to 80° C. over a period of about 30 minutes while stirring and then maintaining the temperature between 60° and 85° C. for about 1 to 5 hours after completion of the addition. The reaction mixture is then added to aqueous caustic to precipitate the product. The crude product is filtered and recrystallized from a suitable solvent such as isopropanol, acetone, toluene, mixtures of isopropanol and water, and the like, to obtain the desired optically pure product.

In another method, either d- or l-2-amino-1-butanol is reacted with an appropriate benzaldehyde (IV) to give an intermediate Schiff base (V), which is subsequently catalytically reduced to the desired optically active 2-(benzylamino)-1-butanol, as illustrated below, wherein X is as previously defined.

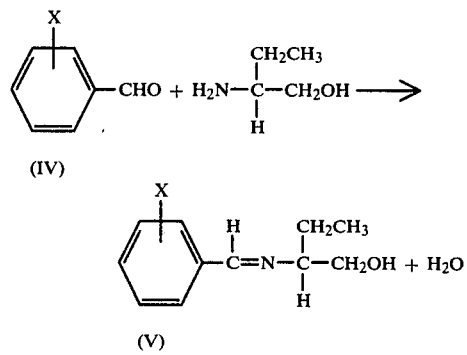

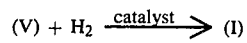

The preparation of dextrorotatory 2-amino-1-butanol is described by Halmos et al. in U.S. Pat. No. 3,553,257. The preparation of levorotatory 2-amino-1-butanol is described in Beilstein 4, 291.

The following examples further illustrate the invention. All parts and percentages are by weight unless otherwise specified.

Unless otherwise indicated, optical rotations were measured by dissolving 1.25, 2.5, 3.0, 4.0, or 5.0 grams of the compound in 100 mls. of methanol and determining the rotation of the plane of a sodium D line at 25° C.

EXAMPLE 1

Formation and Isolation of D-(−)-2-(4-Chlorobenzylamino)-1-Butanol-(−)-Mandelate A stirred mixture of DL-mandelic acid (152 grams; 0.999 mole), 750 mls of water, 1000 mls of isopropyl acetate and D-(−)-2-(4-chlorobenzylamino)-1-butanol (213 grams; 0.997 mole) is heated to 45° C. to effect clarification, slowly cooled to 25° C., seeded with D-(−)-2-(4-chlorobenzylamino)-1-butanol (−)mandelate and slowly cooled to 5° C. over a period of about 2 hours to crystallize D-(−)-2-(4-chlorobenzylamino)-1-butanol (−)mandelate from the reaction mixture. The crystals are recovered by filtration, washed with 100 mls of isopropyl acetate (25° C.) and 100 mls of water (25° C.), and dried to obtain 179.1 grams of crude product.

The crude product is slurried in 300 mls of water (50° C.) and the resulting slurry is cooled to 5° C. and filtered. The recovered crystals are washed with 50 mls of water (5° C.) and dried to obtain 153.6 grams (84% of theoretical) of pure D-(−)-2-(4-chlorobenzylamino)-1-butanol-(−)-mandelate, $[\alpha]_D^{25} = -36.25°$ (C=4; in methanol).

The two-phase filtrate and wash liquors obtained from the filtration of the crude product are combined with the filtrate and wash liquors obtained from the isolation of the pure product and shaken with 15 mls of 50% aqueous sodium hydroxide at room temperature until clear. The mixture is allowed to settle and the aqueous layer, about 1020 mls, containing the sodium salt of L-(+)-mandelic acid, is separated. This solution is saved for subsequent racemization. The isopropyl acetate layer is utilized in Example 2.

In the manner described above substituting ethyl acetate, n-propyl acetate, ethyl propionate, n-propyl propionate, or isopropyl propionate, or mixtures thereof, for the isopropyl acetate similar results are obtained.

EXAMPLE 2

Hydrolysis of D-(−)-2-(4-Chlorobenzylamino)-1-Butanol (−) Mandelate

The isopropyl acetate layer from Example 1 is mixed with D-(−)-2-(4-chlorobenzylamino)-1-butanol (−) mandelate (152.6 grams; 0.42 mole) and 172 mls of 10% aqueous sodium hydroxide, shaken at 30° C. until clarified, and allowed to settle. The aqueous layer, which contains sodium D-(−)-mandelate, is separated and saved for subsequent processing. The organic layer is washed twice with 15 mls of water and the aqueous washings are combined with the above-mentioned aqueous layer.

The water-washed isopropyl acetate layer, now containing about 0.99 mole of D-(—)-2-(4-chlorobenzylamino)-1-butanol is saved for recycling in Example 5.

EXAMPLE 3

Isolation of D-(—)-Mandelic Acid

The combined aqueous layer and washings, containing the sodium D-(—)-mandelate from Example 2, is reacted with oxalic acid dihydrate (53 grams; 0.42 mole) at 50° C. to form sodium acid oxalate which crystallizes from the solution. The resulting slurry is diluted with 400 mls of acetone, cooled to 25° C., and allowed to stand for 2 hours to complete the crystallization. The slurry is filtered to separate the sodium acid oxalate which is then washed with 80 mls of acetone and dried. The filtrate is combined with the acetone wash liquor, concentrated to about 200 mls and then cooled to 5° C. to crystallize the D-(—)-mandelic acid. The resulting slurry is filtered and the solid is washed with 50 mls of water (5° C.) and dried to obtain 45.5 grams (71.2% of theoretical) of D-(—)-mandelic acid: m.p. 131°–133° C.; $[\alpha]_D^{25} = -153.8°$ (C, 4 in water). The overall yield from the D, L-mandelic acid is 59.9% of theoretical.

In the manner of Example 3 substituting equimolecular amounts of tartaric, maleic, fumaric, or malonic acid for the oxalic acid similar results are obtained.

In the manner of Example 3 substituting methanol, ethanol, n-propanol or isopropanol for the acetone similar results are obtained.

EXAMPLE 4

Racemization of Sodium L-(+)-Mandelate

The aqueous solution of sodium L-(+)-mandelate from Example 1 is mixed with 45 mls of 50% aqueous sodium hydroxide, heated to boiling and concentrated to about 1100 mls, then refluxed for 20 hours. At the end of this period the sodium L-(+)-mandelate is completely racemized; $[\alpha]_D^{25} = 0°$ (C, 4 in water).

The solution is then neutralized to pH 7 by adding concentrated hydrochloric acid thereto, and reacted at 50° C. by slowly adding a solution of calcium chloride monohydrate (33 grams; 0.255 mole) in 20 mls of water. The resulting reaction mixture is cooled to 25° C. and filtered to recover the solid. The recovered solid is washed free of chloride ion with water and dried to obtain 79 grams (92.3% of theoretical) of calcium D, L-mandelate.

The racemic calcium mandelate, which is equivalent to 0.46 mole of D, L-mandelic acid, is reacted with oxalic acid dihydrate (29 grams; 0.23 mole) in 500 mls of water at 55° C. to form calcium oxalate which crystallizes out. The resulting slurry is cooled to 25° C. and the calcium oxalate is separated by filtration and washed with 250 mls of water. The filtrate, which now contains about 0.46 mole of D, L-mandelic acid is combined with the water wash liquor and saved for use in Example 5.

EXAMPLE 5

Recycle of D, L-Mandelic Acid and D-(—)-2-(4-Chlorobenzylamino)-1-Butanol

The water-washed isopropyl acetate solution from Example 2, containing about 0.99 mole of recovered D-(—)-2-(4-chlorobenzylamino)-1-butanol, is mixed with the filtrate plus water wash from Example 4, containing 0.46 mole of D, L-mandelic acid, and fresh D, L-mandelic acid (82 grams; 0.54 mole) is added thereto. The mixture is stirred at 30° C. until clarified, seeded with D-(—)-2-(4-chlorobenzylamino)-1-butanol (—) mandelate, slowly cooled to 10° C. over 1½ hours and filtered. The crystals are washed with 125 mls of isopropyl acetate and 250 mls of water, and dried to obtain 163 grams of crude D-(—)-2-(4-chlorobenzylamino)-1-butanol (—) mandelate.

The crude product is slurried in 250 mls of water at 55° C. and the slurry is cooled to 10° C. and filtered. The recovered crystals are washed with 50 mls of water (5° C.) and dried to obtain 153.6 grams (84% of theoretical) of D-(—)-2-(4-chlorobenzylamino)-1-butanol (—) mandelate, $[\alpha]_D^{25} = -35.75°$ (C, 4 in methanol).

EXAMPLES 6–28

In the manner described in Example 1 substituting 0.997 mole of the appropriate 2-(benzylamino)-1-butanol for D-(—)-2-(4-chlorobenzylamino)-1-butanol the optically active mandelate salts of Table I are prepared. Hydrolysis of the mandelate salt in the manner of Example 2 and isolation in the manner of Example 3 is productive of D-(—) or L-(+)-mandelic acid, depending on the salt selected.

TABLE I

| Example | Starting 2-(Benzylamino)-1-Butanol | Product |
| --- | --- | --- |
| 6 | D-(—)-2-(4-fluorobenzylamino)-1-butanol | D-(—)-2-(4-fluorobenzylamino)-1-butanol-(—)-mandelate |
| 7 | L-(+)-2-(4-chlorobenzylamino)-1-butanol | L-(+)-2-(4-chlorobenzylamino)-1-butanol-(+)-mandelate |
| 8 | L-(+)-2-(4-bromobenzylamino)-1-butanol | L-(+)-2-(4-bromobenzylamino)-1-butanol-(+)-mandelate |
| 9 | D-(—)-2-(3-chlorobenzylamino)-1-butanol | D-(—)-2-(3-chlorobenzylamino)-1-butanol-(—)-mandelate |
| 10 | L-(+)-2-(3-chlorobenzylamino)-1-butanol | L-(+)-2-(3-chlorobenzylamino)-1-butanol-(+)-mandelate |
| 11 | D-(—)-2-(3-bromobenzylamino)-1-butanol | D-(—)-2-(3-bromobenzylamino)-1-butanol-(—)-mandelate |
| 12 | L-(+)-2-(3-bromobenzylamino)-1-butanol | L-(+)-2-(3-bromobenzylamino)-1-butanol-(+)-mandelate |
| 13 | D-(—)-2-(3-fluorobenzylamino)-1-butanol | D-(—)-2-(3-fluorobenzylamino)-1-butanol-(—)-mandelate |
| 14 | L-(+)-2-(3-fluorobenzylamino)-1-butanol | L-(—)-2-(3-fluorobenzylamino)-1-butanol-(+)-mandelate |
| 15 | D-(—)-2-(2-fluorobenzylamino)-1-butanol | D-(—)-2-(2-fluorobenzylamino)-1-butanol-(—)-mandelate |
| 16 | L-(+)-2-(2-fluorobenzylamino)-1-butanol | L-(+)-2-(2-fluorobenzylamino)-1-butanol-(+)-mandelate |
| 17 | D-(—)-2-(2-chlorobenzylamino)-1-butanol | D-(—)-2-(2-chlorobenzylamino)-1-butanol-(—)-mandelate |
| 18 | L-(+)-2-(2-chlorobenzylamino)-1-butanol | L-(+)-2-(2-chlorobenzylamino)-1-butanol-(+)-mandelate |
| 19 | D-(—)-2-(2-bromobenzylamino)-1-butanol | D-(—)-2-(2-bromobenzylamino)-1-butanol-(—)-mandelate |
| 20 | L-(+)-2-(2-bromobenzylamino)-1-butanol | L-(+)-2-(2-bromobenzylamino)-1-butanol-(+)-mandelate |
| 21 | D-(—)-2-(4-nitrobenzylamino)-1-butanol | D-(—)-2-(4-nitrobenzylamino)-1-butanol-(—)-mandelate |
| 22 | L-(+)-2-(4-nitrobenzylamino)-1-butanol | L-(+)-2-(4-nitrobenzylamino)-1-butanol-(+)-mandelate |
| 23 | D-(—)-2-(3-nitrobenzylamino)-1-butanol | D-(—)-2-(3-nitrobenzylamino)-1-butanol-(—)-mandelate |
| 24 | L-(+)-2-(3-nitrobenzylamino)-1-butanol | L-(+)-2-(3-nitrobenzylamino)-1-butanol-(+)-mandelate |
| 25 | D-(—)-2-(2-nitrobenzylamino)-1-butanol | D-(—)-2-(2-nitrobenzylamino)-1-butanol-(—)-mandelate |
| 26 | L-(+)-2-(2-nitrobenzylamino)-1-butanol | L-(+)-2-(2-nitrobenzylamino)-1-butanol-(+)-mandelate |
| 27 | L-(+)-2-(4-fluorobenzylamino)-1-butanol | L-(+)-2-(4-fluorobenzylamino)-1-butanol-(+)-mandelate |

TABLE I-continued

| Example | Starting 2-(Benzylamino)-1-Butanol | Product |
|---|---|---|
| 28 | D-(−)-2-(4-bromobenzylamino)-1-butanol | D-(−)-2-(4-bromobenzylamino)-1-butanol-(−)-mandelate |

I claim:

1. A process for resolving DL-mandelic acid which comprises:
    (a) reacting about equimolecular amounts of DL-mandelic acid and an optically active 2-benzylamino-1-butanol represented by formula (I),

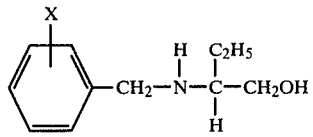

wherein X represents chloro, bromo, fluoro, or nitro, at about 40°–50° C. in a two-phase mother liquor, consisting of a mixture of a water phase and a water immiscible organic phase, said organic phase being a lower alkyl ester of a lower aliphatic carboxylic acid selected from ethyl acetate, n-propyl acetate, isopropyl acetate, ethyl propionate, n-propyl propionate, or isopropyl propionate, or mixtures thereof, to form a mandelate salt represented by formula (II),

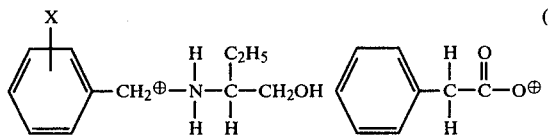

(b) cooling the reaction mixture to crystallize said mandelate salt;
   (c) separating the crude mandelate salt from the two-phase mother liquor;
   (d) recrystallizing or slurrying the crude mandelate salt in a solvent medium selected from water, methanol, ethanol, or isopropanol, or mixtures thereof, to obtain an optically pure mandelate salt;
   (e) alkalizing the water phase of the two-phase mother liquor obtained in step (c);
   (f) separating the alkalized water phase from the organic phase;
   (g) agitating the optically pure mandelate salt from step (d) and the organic phase from step (f) with about 1.05 to 1.10 moles of aqueous sodium or potassium hydroxide per mole of mandelate salt at ambient temperature to hydrolyze said salt and form a clear two-phase liquid mixture consisting of an organic phase containing an optically active compound of formula (I) and an alkalized aqueous phase containing the sodium or potassium salt of an optically active mandelic acid;
   (h) recovering the aqueous phase from step (g) and reacting said salt of an optically active mandelic acid with about an equimolecular amount of an organic dicarboxylic acid selected from oxalic, tartaric, maleic, malonic, or fumaric acid, at about 25°–40° C. to form a mixture of an optically active mandelic acid and a mono-sodium or potassium salt of said dicarboxylic acid having a low solubility in water;
   (i) cooling the reaction mixture to ambient temperature and diluting the same with a water-soluble organic liquid solvent selected from the group consisting of acetone, methanol, ethanol, n-propanol, and isopropanol to complete the precipitation of said salt of said dicarboxylic acid;
   (j) separating said salt of said dicarboxylic acid;
   (k) removing said water-soluble organic solvent; and
   (l) recovering D-(−) or L-(+)-mandelic acid from said mother liquor.

2. The process of claim 1 wherein step (a) is reacting about equimolecular amounts of DL-mandelic acid and a compound of formula (I) wherein X represents chloro, bromo, or fluoro at a temperature of about 40°–50° C. in a mixture of water and isopropyl acetate; step (b) is cooling to a temperature of about 0°–25° C. over a period of about 1–2 hours; step (d) is slurrying said crude mandelate salt in water at about 25°–30° C. and then cooling it to about 0°–20° C.; the step (e) is alkalizing the water phase of said two-phase mother liquor to a pH of at least 12; step (g) is agitating said optically pure mandelate salt and said organic phase with an amount of 50% by weight aqueous sodium hydroxide to provide between about a 5–10% molecular excess of said sodium hydroxide after complete hydrolysis of said mandelate salt; step (h) is reacting said salt of an optically active mandelic acid with an equimolecular amount of oxalic acid at a temperature of about 25°–40° C.; and step (i) is cooling the reaction mixture to a temperature of about 20°–25° C. and diluting the same with acetone to complete the precipitation of monosodium oxalate and cooling the essentially acetone-free mother liquor to a temperature of about 0°–10° C. to crystallize D-(−) or L-(+)-mandelic acid.

3. The process of claim 2 wherein step (a) is reacting about equimolecular amounts of DL-mandelic acid and D-(−)-2-(4-chlorobenzylamino)-butanol; step (b) is cooling to a temperature of about 5°–10° C.; step (d) is slurrying said crude mandelate salt at a temperature of about 25°–30° C. and the cooling it to about 5°–10° C. to obtain D-(−)-2-(4-chlorobenzylamino)-1-butanol-(−)-mandelate; step (e) is alkalizing said water phase to a pH of about 13; step (g) is agitating said D-(−)-2-(4-chlorobenzylamino)-1-butanol-(−)-mandelate and said organic phase; step (h) is reacting at a temperature of about 30°–35° C.; and step (i) is cooling the reaction mixture to a temperature of about 20°–25° C. and diluting the same with acetone to complete the precipitation of monosodium oxalate and cooling the essentially acetone-free mother liquor to a temperature of about 0°–5° C. to crystallize D-(−)-mandelic acid.

4. The process of claim 1 wherein step (f) is separating the alkalized water phase from the organic phase, heating said water phase at reflux temperature until racemization is complete and acidifying the resulting solution.

5. The process of claim 4 wherein the DL-mandelic acid used in step (a) is obtained from the racemized water phase of step (f).

6. The process of claim 1 wherein the optically active 2-(benzylamino)-1-butanol used in step (a) is obtained from said organic phase containing an optically active compound of formula (I) of step (g).

* * * * *